United States Patent [19]
Weinel

[11] Patent Number: 5,321,266
[45] Date of Patent: Jun. 14, 1994

[54] PNEUMATIC TWO-LAYER DETECTOR FOR NDIR GAS ANALYZERS

[75] Inventor: Johann Weinel, Karlsruhe, Fed. Rep. of Germany

[73] Assignee: Siemens Aktiengesellschaft, Munich, Fed. Rep. of Germany

[21] Appl. No.: 39,110
[22] PCT Filed: Oct. 2, 1991
[86] PCT No.: PCT/DE91/00776
§ 371 Date: Apr. 12, 1993
§ 102(e) Date: Apr. 12, 1993
[87] PCT Pub. No.: WO92/07247
PCT Pub. Date: Apr. 30, 1992

[30] Foreign Application Priority Data

Oct. 11, 1990 [DE] Fed. Rep. of Germany ... 9014162[U]

[51] Int. Cl.$^5$ .............................................. G01N 21/61
[52] U.S. Cl. ....................................... 250/344; 250/345
[58] Field of Search ........................ 250/344, 345, 346

[56] References Cited

U.S. PATENT DOCUMENTS

| | | |
|---|---|---|
| 4,288,693 | 9/1981 | Fabinski et al. ............... 250/345 |
| 4,468,561 | 8/1984 | Speeter ......................... 250/345 |
| 4,742,229 | 5/1988 | Weinel ........................... 250/343 |

FOREIGN PATENT DOCUMENTS

| | | |
|---|---|---|
| 0213304 | 3/1987 | European Pat. Off. . |
| 1017385 | 10/1957 | Fed. Rep. of Germany . |
| 1109418 | 6/1961 | Fed. Rep. of Germany . |
| 2702978 | 8/1977 | Fed. Rep. of Germany . |
| 2638522 | 3/1978 | Fed. Rep. of Germany . |
| 2127853 | 10/1972 | France . |

*Primary Examiner*—Carolyn E. Fields
*Attorney, Agent, or Firm*—Kenyon & Kenyon

[57] ABSTRACT

Two gas-filled chambers (K1, K2) arranged one behind the other in the beam path, with frontal areas (F) transparent to the beam, are interconnected by a first line (L12) which contains a first pressure or flow rate sensor (SF1). A buffer space (P) is connected to one of the two chambers (K1) via a second line (L11) in which is arranged a second pressure or flow rate sensor (SF2). The output signals from both flow rate sensors (SF1, SF2) are taken via amplifiers (V1, V2) to a differentiator. The degree of amplification of at least one amplifier (V2) is tunable for equalizing. The field of application of the invention is in gas analyzers operating on the infrared absorption system.

6 Claims, 1 Drawing Sheet

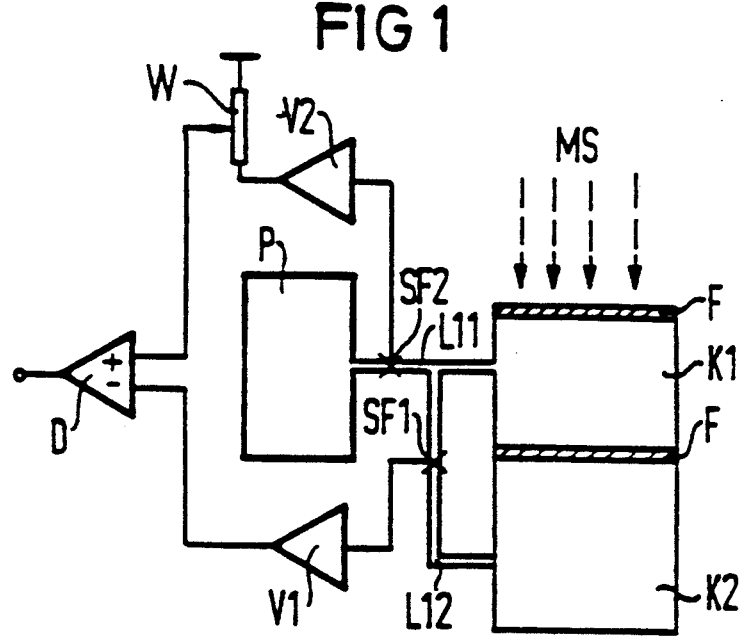
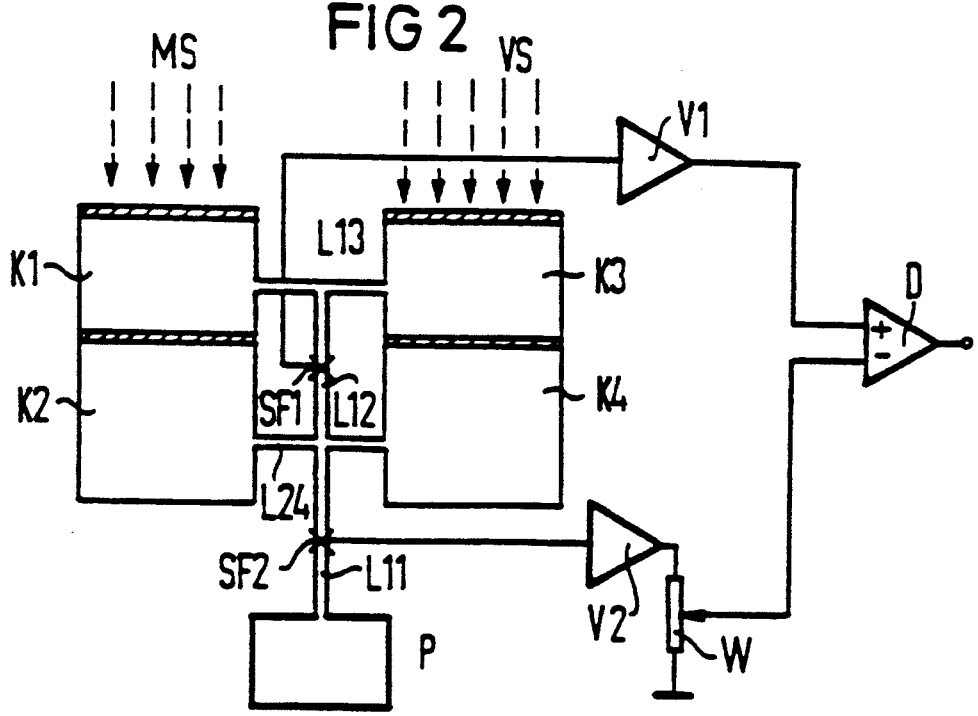

PNEUMATIC TWO-LAYER DETECTOR FOR NDIR GAS ANALYZERS

BACKGROUND OF THE INVENTION

The present invention relates to a pneumatic, two-layer detector for use in NDIR (Non-dispersive Infrared) gas analyzers having two, coaxially arranged, gas-filled chambers with radiation permeable frontal areas, a line which couples the chambers, and a pressure or flow-rate sensor of a pneumo-electrical transducer arranged in the line.

These types of detectors are employed in gas analyzers, in which modulated infrared (IR) radiation strikes the detector through a cuvette filled with the gas being analyzed. As a rule, the gas being analyzed is a gas mixture having one or more components to be evaluated. The components to be evaluated or a gas having the same kind of absorptive capacity for IR-radiation constitute the gas filling in the detector chambers (see, e.g., German Patent 1 017 385).

Distortions in the measuring-signal occur because of so-called "cross sensitivity". That is, there are instances when the absorption bands of other components contained in the gas being analyzed overlap with those of the component to be measured. The known two-layer detector configuration, in which the two chambers are pneumatically connected back to back, improves the selectivity ratio. In this manner, the sensitivity due to the absorption bands of all disturbing components may be reduced but can not be totally eliminated. Thus there is a need for a detector for use in a gas analyzer which eliminates cross-sensitivity due to the absorption bands of other components contained in the gas being analyzed.

SUMMARY OF THE INVENTION

The present invention meets the aforementioned need by providing a pneumatic two-layer detector, which comprises two chambers, two lines, two pneumo-electric assemblies, a buffer volume, and a differential element. The first and second chambers are adapted to be filled with a gas and have a radiation permeable frontal window. Further, the two chambers are coaxial. The first line couples the first chamber with the second chamber. The first pneumo-electrical transducer includes a pressure or flow rate sensor arranged in the first line and provides an output. The second line couples at least one of the first and second chambers with the buffer volume. The second pneumo-electrical transducer includes a pressure or flow rate sensor arranged in the second line, is adapted to provide an output, and includes means for adjusting the amplification of its output. The differential element has inputs electrically coupled with the outputs of the first and said second pneumo-electrical transducers. Not only does the present invention further reduce the sensitivity to disturbing components, but it also selectively compensates one of these disturbing components to zero. The present invention does so electrically, by attenuating the signal coming from the second pneumo-electrical transducer before forming the differential. In this manner, the detector becomes insensitive to this disturbing gas.

BRIEF DESCRIPTION OF THE DRAWINGS

FIG. 1 schematically depicts an exemplified embodiment of the present invention.

FIG. 2 schematically depicts an alternative embodiment in which a two-beam variant of an NDIR gas analyzer includes detectors according to the present invention.

DETAILED DESCRIPTION

As shown in FIG. 1, a two-layer detector has two chambers K1 and K2, which are arranged coaxially, one behind the other. The frontal area of each chamber is provided with a radiation permeable window F. The chambers K1 and K2 are filled with the gas to be analyzed or with another gas having the same kind of absorptivity. Modulated radiation from the measuring path of rays MS enters through the window F into the chambers K1 and K2. The radiant energy is absorbed by the gas contained therein. This absorbed radiant energy leads to a warming of the gas and, thus, to an increase in pressure of the gas in the chambers. A flow-rate sensor SF1, which operates based on the anemometer principle, is arranged in a line L12 which couples the chambers K1 and K2. Together with the amplifier V1, this flow-rate sensor SF1 constitutes a component of a pneumo-electrical transducer.

A buffer volume P is connected to the first chamber K1 via the coupling line L11. A second flow-rate sensor SF2 is arranged in the coupling line L11, and, together with the amplifier V2, constitutes a component of a pneumo-electrical transducer. The amplification and thus the amplitude of the output signal from the amplifier V2 can be adjusted via a potentiometer W. The output signals from the amplifiers V1 and V2 (as adjusted by W) are fed to a differential element D, which provides a measuring signal at its output. This measuring signal is substantially free of the influences of the disturbing absorption bands of components of the measuring gas mixture because of the pneumatic differential connection of the chambers, and is completely liberated of these influences for a certain disturbing gas because of the electrical differential formed.

FIG. 2 depicts the application of a detector according to the present invention in a two-beam NDIR analyzer. The two-beam NDIR analyzer includes two coaxially arranged chambers K1, K2 in the measuring path of rays MS and two coaxially arranged chambers K3, K4 in the comparative path of rays VS. The chambers K1 and K3 are coupled via line L13, and the chambers K2 and K4 are coupled via line L24. A first flow-rate sensor SF1 is arranged in a cross link L12 which couples lines L13 and L24. The first flow-rate sensor SF1 and the amplifier V1 constitute a component of a pneumo-electrical transducer.

A coupling line L11 is connected to the line L24 at one end and to a buffer volume P at its other end. A second flow-rate sensor SF2 is arranged in line L11 and is part of a second pneumo-electrical transducer whose amplification is adjustable by the amplifier V2 and potentiometer W. As previously described, the output signals from the amplifiers V1 and V2 are fed to a differential element D.

Depending on the application, in a single-beam embodiment of the present invention such as the one illustrated in FIG. 1, the chamber K2 can also be optionally coupled via a line containing the second flow-rate sensor SF2 to the buffer volume P. Correspondingly, in a two-beam embodiment of the present invention such as the one illustrated in FIG. 2, the buffer volume P and, thus, the second flow-rate sensor SF2 can be coupled to the line L13 interconnecting chambers K1 and K3.

I claim:

1. A pneumatic two-layer detector for non-dispersive infrared gas analyzers comprising:
   a) a first chamber adapted to be filled with a gas and having a radiation permeable frontal window;
   b) a second chamber adapted to be filled with a gas, having a radiation permeable frontal window, and being coaxial with said first chamber;
   c) a first line coupling said first chamber with said second chamber;
   d) a first pneumo-electrical transducer including a sensor arranged in said first line, and being adapted to provide an output;
   e) a buffer volume;
   f) a second line coupling at least one of said first chamber and said second chamber with said buffer volume;
   g) a second pneumo-electrical transducer including a sensor arranged in said second line, being adapted to provide an output;
   h) means for adjusting the amplification of said output of said second pneumo-electrical transducer; and
   i) a differential element having inputs electrically coupled with said outputs of said first pneumo-electrical transducer and the adjusted second pneumo-electrical transducer.

2. The detector of claim 1 wherein said sensor of said first pneumo-electrical transducer is a pressure sensor and wherein said sensor of said second pneumo-electrical transducer is a pressure sensor.

3. The detector of claim 1 wherein said sensor of said first pneumo-electrical transducer is a flow-rate sensor and wherein said sensor of said second pneumo-electrical transducer is a flow-rate sensor.

4. A pneumatic two-layer detector for two-beam, non-dispersive infrared gas analyzers employing first and second incident radiation comprising:
   a) a first chamber adapted to be filled with gas and having a radiation permeable window facing the first incident radiation employed;
   b) a second chamber adapted to be filled with gas, being coaxially arranged with said first chamber, and having a radiation permeable window facing the first incident radiation employed;
   c) a third chamber adapted to be filled with gas and having a radiation permeable window facing the second incident radiation employed;
   d) a fourth chamber adapted to be filled with gas, being coaxially arranged with said third chamber, and having a radiation permeable window facing the second incident radiation employed;
   e) a first line coupling said first chamber with said third chamber;
   f) a second line coupling said second chamber with said fourth chamber;
   g) a third line coupling said first line with said second line;
   h) a buffer volume;
   i) a fourth line coupling one of said first line or said second line with said buffer volume;
   j) a first pneumo-electrical transducer having a sensor arranged in said third line, and adapted to provide an output;
   k) a second pneumo-electrical transducer having a sensor arranged in said fourth line, adapted to provide an output;
   l) means for adjusting the amplification of said output of said second pneumo-electrical transducer; and
   m) a differential element having inputs electrically coupled with said outputs of said first pneumo-electrical transducer and said second pneumo-electrical transducer.

5. The detector of claim 4 wherein said sensor of said first pneumo-electrical transducer is a pressure sensor and wherein said sensor of said second pneumo-electrical transducer is a pressure sensor.

6. The detector of claim 4 wherein said sensor of said first pneumo-electrical transducer is a flow-rate sensor and wherein said sensor of said second pneumo-electrical transducer is a flow-rate sensor.

* * * * *